(12) United States Patent
Jessop (10) Patent No.: US 7,320,259 B2
(45) Date of Patent: Jan. 22, 2008

(54) PIPETTE TIP FOR EASY SEPARATION

(75) Inventor: Paul M. Jessop, Hildale, UT (US)

(73) Assignee: Medax International, Inc., Salt Lake City, UT (US)

( * ) Notice: Subject to any disclaimer, the term of this patent is extended or adjusted under 35 U.S.C. 154(b) by 305 days.

(21) Appl. No.: 11/068,210

(22) Filed: Feb. 28, 2005

(65) Prior Publication Data

US 2005/0204832 A1    Sep. 22, 2005

(51) Int. Cl.
B01L 3/02 (2006.01)
(52) U.S. Cl. .................................. 73/864.11
(58) Field of Classification Search ............. 73/864.01, 73/864.11–864.18; 422/100; 436/180
See application file for complete search history.

(56) References Cited

U.S. PATENT DOCUMENTS 5,200,151 A * 4/1993 Long .......................... 422/100
5,342,482 A    8/1994 Duesel
6,499,363 B1   12/2002 Morimoto et al.
2003/0209090 A1  11/2003 Blaszcak et al.
2004/0011145 A1   1/2004 Blaszcak et al.

OTHER PUBLICATIONS

PCT International Search Report, mailed Feb. 13, 2007, PCT/US06/07005.
PCT Written Opinion, mailed Feb. 13, 2007, PCT/US06/07005.

* cited by examiner

*Primary Examiner*—Robert Raevis
(74) *Attorney, Agent, or Firm*—Holme Roberts & Owen LLP (57) ABSTRACT

A pipette tip is provided including sidewall having a distal end and a proximal end. The sidewall extends from the proximal end to the distal end and defines a surface around a center axis. The distal portion defines a tip having an aperture. The proximal portion has a sealing member and a wall member spaced apart and defining a channel therein between. The sealing member is deflectable from a first position to a second position when receiving the shaft of a pipette tool. The sealing member is elastically deformable so as to creates a seal with the shaft.

11 Claims, 7 Drawing Sheets

PIPETTE TIP FOR EASY SEPARATION

CROSS REFERENCE TO RELATED APPLICATIONS

Not applicable.

BACKGROUND OF THE INVENTION

1. The Field of the Invention

The present invention generally relates to a pipette tip, more specifically the invention relates to a pipette tip capable of easy expulsion from a pipette tools.

2. The Relevant Technology

Medical and research laboratories have used pipette tools with disposable tips to perform tests on biological samples. These tests require repetitive steps that are numerous. For example, large quantities of routine blood tests may be performed by a laboratory technician at one time. Samples of the blood in test tubes may be arranged in an array to facilitate speed in performance of the tests. Specific chemical or biological materials or reagents are then added to each tube in like amounts as a part of the testing process. This is typically accomplished by drawing in and subsequently injecting the chemical or biological material or the reagent through a pipette tip that is attached to a pipette tool.

For testing of arrays of test tubes, multi-site pipette tools are provided that can hold multiple pipette tips. That is, manufactures of pipette tips provide them on trays or racks in an array (see U.S. Pat. No. 3,853,217 to Scordato and U.S. Pat. No. 5,324,482 to Scaramella, et al.) so that a multi-site pipette tool may easily register with sets of pipette tips. The pipette tips are typically thrown away after use.

The disposable pipette tips are typically supplied in trays which have openings for receiving 96 pipette tips. U.S. Pat. No. 5,324,482 to Scaramella, et al. shows a system for storing pipette tips. It uses an alignment plate that is attached to a transfer card by a locking mechanism. The pipette tips are stored on the transfer card and a stack of transfer cards with pipette tips are positioned in a box for transport and sale along with an alignment plate.

The pipette tips are sometimes difficult to remove from the pipette tool. When the pipette tip does not easily eject from the pipette tip, the technicians may shake, tap or use additional force to separate the pipette tip from the pipette tool. Thus, the technicians lose valuable time if the pipette tip sticks to the pipette tool, especially due to the repetitive nature of the tests.

In view of the above and other related drawbacks and limitations identified in the relevant pipette tips, there is a need for a pipette tip that allows a quick separation from a pipette tool.

BRIEF SUMMARY OF THE INVENTION

In various exemplary embodiments of the present invention, a pipette tip is provided. The pipette tip comprises a tapered sidewall having a proximal end, a distal end and a sidewall length extending from the proximal end to the distal end. The sidewall has an arcuate inner surface that extends along the length The arcuate inner surface defines a volume with an axis. The axis extends from the proximal end of the sidewall to the distal end. The sidewall has an upper portion for receiving a shaft of a pipette tool.

The upper portion of the sidewall comprises a wall member having a wall member length, a wall member channel surface and an outer wall member surface and a top surface. The upper portion also has a sealing member having a sealing member length, a sealing member channel surface and an sealing member inner surface. The sealing member channel surface is spaced from the wall member channel surface so as to define an arcuate channel therein between. The arcuate channel extends from the top surface toward the distal end. The sealing member is deflectable from a first position to a second position in the direction of the arcuate channel when receiving a shaft of a pipette tool. The sealing member is also elastically deformable so as to frictionally effect a seal around the shaft of the pipette tool. The pipette tip also has a stop means positioned in the upper portion for limiting the travel of the shaft of the pipette tool toward the distal end.

In another embodiment, the length of the wall member and the length of the sealing member are measured relative to a bottom surface of the channel.

In yet another embodiment, the stop means is located on the inner surface of the tapered sidewall at a distance below the sealing member. In this location, the stop means is configured to prevent the shaft from contacting the inner surface between the distal end and the stop means.

In another embodiment, the sealing member length is proximate to the wall member length.

In still another embodiment, the sealing member length is equal to the wall member length.

In yet another embodiment, the wall member channel surface has a straight surface segment and a tapered surface segment. The tapered surface segment having a width defined by the distance from the outer wall member surface to the tapered surface segment in the radial direction. The width increases from the proximal end to the distal end.

In still another embodiment, the channel has a bottom surface joining the wall member channel surface and the sealing member channel surface and the wall member channel surface has a straight surface segment and a tapered surface segment. The channel has a first channel section that is essentially rectangular in cross section defined between the flat surface segment and a first section of the sealing member channel surface. The channel has a second channel section that is essentially trapezoidal in cross section defined between the tapered surface segment and a second section of the sealing member channel surface.

These and other features of the present invention will become more fully apparent from the following description and appended claims, or may be learned by the practice of the invention as set forth hereinafter.

BRIEF DESCRIPTION OF THE DRAWING

To further clarify the above and other advantages and features of the present invention, a more particular description of the invention will be rendered by reference to specific embodiments thereof which are illustrated in the appended drawings. It is appreciated that the drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

Reference will now be made in detail to the preferred embodiments of the present invention, examples of which are illustrated in the accompanying drawings. The various exemplary embodiments provide examples of a pipette tip capable of easy expulsion from the pipette tool.

Figure 1:
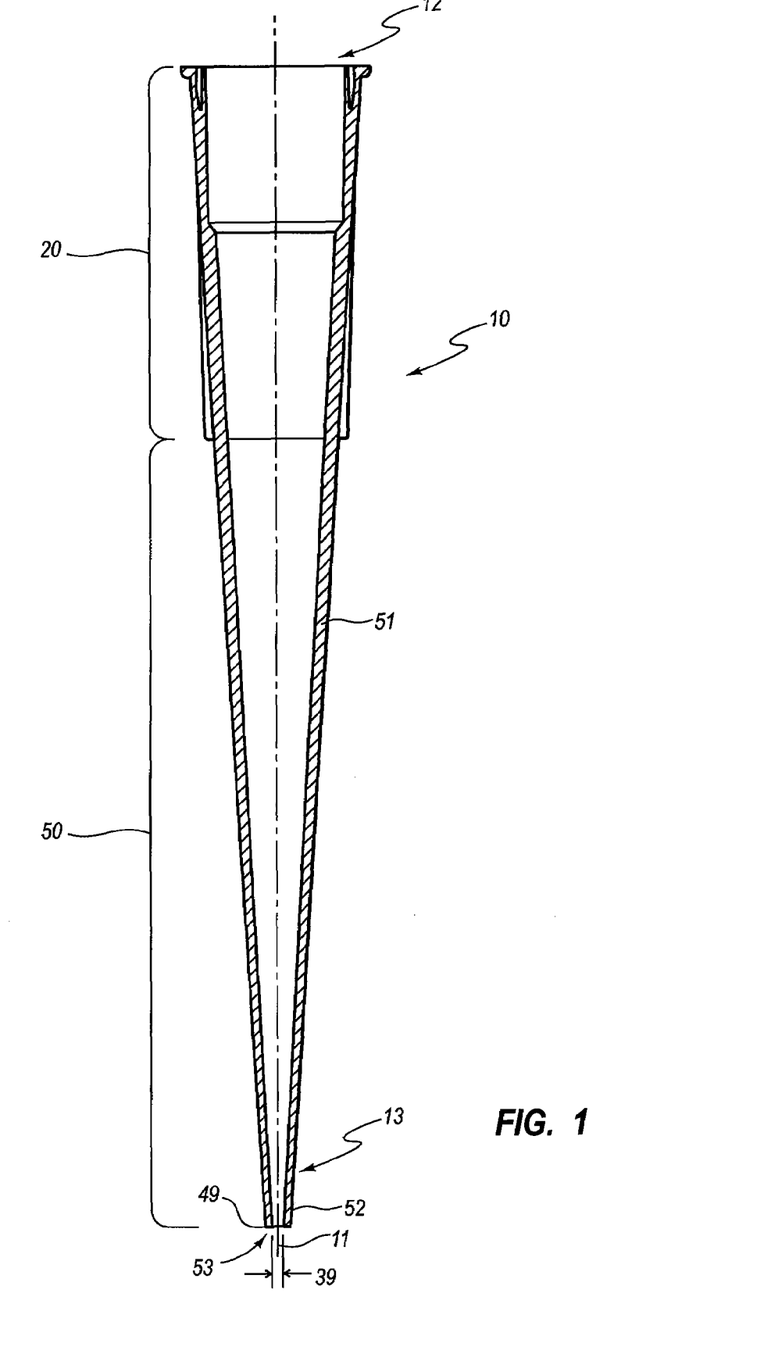
FIG. 1 is a cross sectional view of an embodiment a pipette tip in accordance with the present invention.

One embodiment of a pipette tip 10 is illustrated in FIG. 1 in accordance with the present invention. In one preferred embodiment, the pipette tip 10 having a center axis 11 includes a proximal end 12 and a distal end 13. The proximal end 12 is designed to be attached to the pipette tool. The distal end is designed to extract and inject liquid, such as biological samples. FIG. 1 illustrates the pipette tip 10 including a proximal portion 20 on the proximal end 12 and a distal portion 50 on the distal end 13. The proximal portion 20 illustrated in FIG. 1 is shown having a securing medium for attaching and removing the pipette tip 10 to the pipette tool using minimal force.

Figure 2:
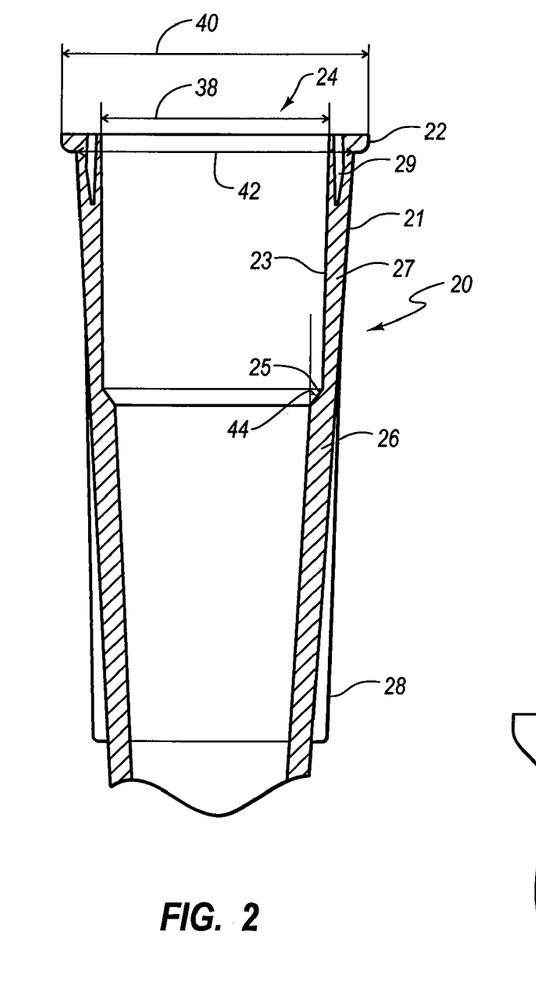
FIG. 2 is a detailed view of a section of a pipette tip in accordance with the present invention.
Figure 3:
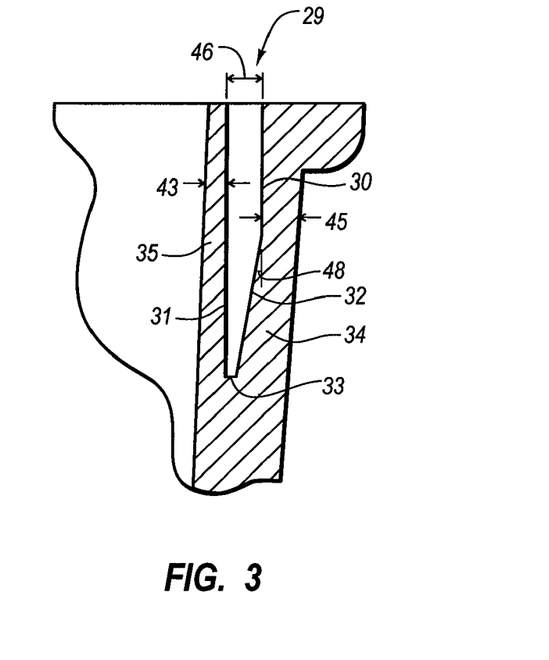
FIG. 3 is a detailed end view of the section of the pipette tip of FIG. 2.

The proximal portion 20 is further illustrated in FIGS. 2-3. The proximal portion 20 includes a sidewall 21 that extends from the proximal end 12 to the distal end 13 and defines a surface around the center axis 11. The sidewall 21 has a generally tapered shape, so as to have a larger diameter 38 at the proximal end 12 and a smaller diameter 39 at the distal end 13. The larger diameter 38 has a diameter at the proximal end 12 that is about 0.22 inches when formed. The proximal portion 20 has a flange 22 that extends around the proximal portion 20 at the proximal end 12. The flange 22 gives the pipette tip 10 extra support and rigidity. The flange 22 may have a radius on a lower corner. The outer diameter 40 of the flange 22 is about 0.29 inches. The outer diameter 42 of the upper sidewall just under the flange is about 0.26 inches.

The side wall 21 includes an inner surface 23 designed to fit tightly against the pipette tool. The inner surface 23 has a slight taper to allow the pipette tool to be inserted easily at the top and tighter at the bottom. The pipette tool is inserted into the proximal portion 20 through an opening 24. A tapered surface 25 in the inner surface 23 provides a stop for the pipette tool when it is inserted up against the tapered surface 25. The tapered surface 25 has an angle 44 measured relative to a horizontal plane at about 30 degrees. The tapered surface 25 divides the proximal portion 20 between a lower sidewall 26 and an upper sidewall 27. The lower side wall 26 extends from the tapered surface 25 to the distal portion 50. The upper sidewall 27 extends from the tapered surface 25 to the flange 22 of the proximal portion 20.

Outer ribs 28 are spaced around the external surface of the sidewall 21 to provide extra rigidity and strength. For example, the outer ribs 28 may include 6 ribs spaced evenly at about 60 degree angles from each other. The cross-section of each rib may be triangular, circular, square or any other like shape to provide structural support for the pipette tip 10. The outer ribs 28 span between the lower sidewall 26 and the upper sidewall 27.

A channel 29 is provided in the proximal portion 20, as detailed in FIG. 3. The channel 29 projects into the upper sidewall 27 from the flange 22. The channel 29 is defined by an outer surface 30, an inner surface 31, an angled surface 32 and a bottom surface 33. The channel 29 has a thickness 46 of about 0.01 inches. The outer surface 30 faces the inner surface 31, which both define the channel 29 having a circular or annular shape. The angled surface 32 extends from the outer surface 30 to the bottom 33 at an angle 48 of about 1 to 2 degrees to provide more flexibility at the top of the channel 29 and more stability at the bottom of the channel 29.

The channel 29 bifurcates the upper sidewall 27 into an outer section 34 and an inner section 35. The outer section 34 has a thickness 45 of about 0.011 inches and the inner section 35 has a thickness 43 of about 0.005 inches. The inner section 35, when cooled from the mold, tends to slightly bend inward toward the center axis 11. This way, when the button on the pipette tool is pushed to eject the pipette tip, the armature pushes against the inner section 35 for easy expulsion from the pipette tool.

The distal portion 50 includes a tapered sidewall 51, as shown in FIG. 1. The tapered sidewall 51 extends from the proximal portion 20 to the distal end 13 and defines a surface around the center axis 11. The tapered sidewall 51 has a generally tapered shape, so as to have a larger diameter 38 at the proximal portion 20 and a smaller diameter 39 at the distal end 13. The smaller diameter 39 has a diameter at the distal end 12 that is about 0.02 inches. The distal end 13 of the tapered sidewall 51 includes an angled tip 52 that has an angle 49 that is preferably in a range of about 9 degrees to about 10 degrees from the center axis 11.

Figure 4:
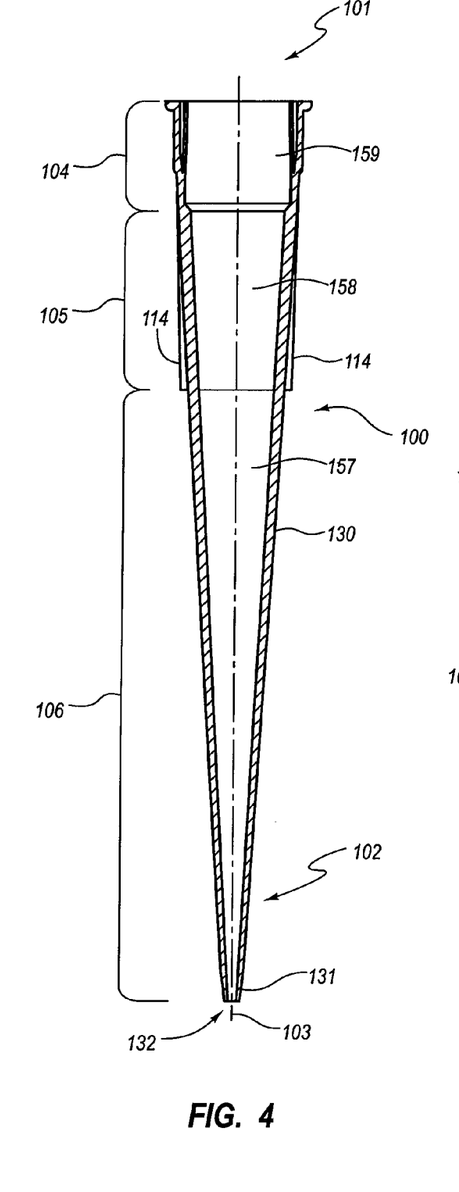
FIG. 4 is a cross sectional view of another embodiment of a pipette tip in accordance with the present invention.

Another embodiment of a pipette tip is illustrated in FIG. 4 in accordance with the present invention. In a preferred embodiment, pipette tip 100 has a proximal end 101, a distal end 102 and an axis 103. Pipette tip 100 has a tapered sidewall 130 having a length that extends between the distal end 102 and the proximal end 101. As shown, pipette tip 100 has an upper portion 104, a middle portion 105 and a lower portion 106. Lower portion 106 has an angled tip 131 with an aperture 132 disposed therein for receiving a fluid such as a reagent or a sample in a laboratory setting. Middle portion 105 has a plurality of ribs 114 that provide structural rigidity to pipette tip 100. The bottom surface of each rib 114 is configured to contact the top surface of a pipette rack (not shown). Upper portion 104 has an opening 110 for receiving the shaft of a pipette tool.

Sidewall 130 tapers or narrows relative to axis 103 from the proximal end 101 to the distal end 102. Tapered sidewall 130 has an arcuate inner surface relative to axis 103 extending along the length of sidewall 130 that defines an interior volume comprising the contiguous volumes identified as distal volume 157, middle volume 158 and proximal volume 159 of pipette tip 100. The combination of distal volume 157 and middle volume 158 is essentially conical in shape.

Preferably, middle volume 157 and distal volume 158 of pipette tip 100 combine to provide a volume ranging from 10 μL to 10 mL for receiving a liquid such as a reagent or a biological sample. However, any size volume may be used for a pipette tip 100 in accordance with the present invention according to the particular needs of a user. Proximal volume 159, as illustrated, is comprised of a first frustoconical portion, a second frustoconical portion and a cylindrical portion that together make up the proximal volume 159.

Figure 5:
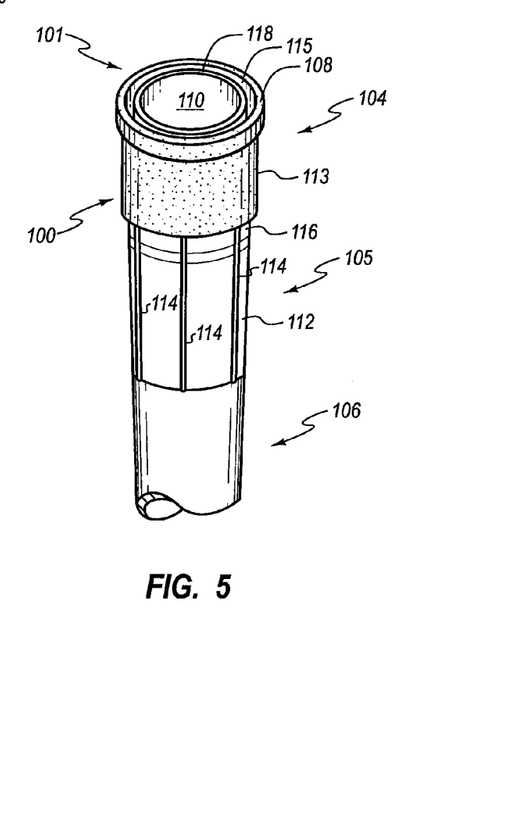
FIG. 5 is a perspective view of the pipette tip of FIG. 4.

FIG. 5 illustrates a cut-away perspective view of pipette tip 100. An opening 110 in upper sidewall portion 104 is configured to receive a pipette tool shaft. Opening 110 is essentially annular and is defined by an arcuate surface of sealing member 118. Generally, upper portion 104 has an outer wall member 108, a channel 115 and a sealing member 118. Annular channel 115 is formed between an arcuate surface of wall member 108 and an arcuate surface of sealing member 118.

Figure 6:
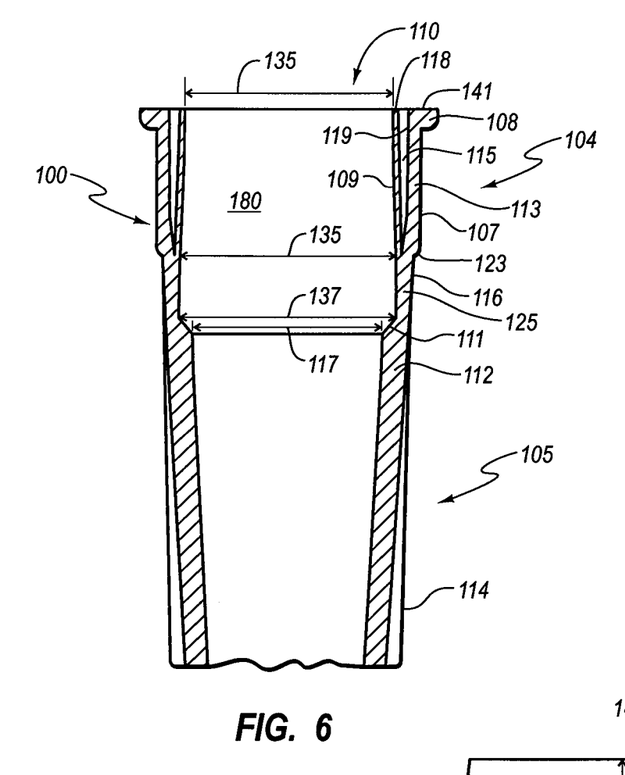
FIG. 6 is a detailed view of a section of the pipette tip of FIG. 4.

Proximal sidewall portion 104 and a section of middle sidewall portion 105 are further illustrated in the cross sectional view of pipette tip 100 shown in FIG. 6. In the illustration, proximal sidewall portion 104 extends from annular groove 117 to opening 110 and is configured to receive a shaft of a pipette tool, the operation of which is further illustrated and described with respect to FIGS. 8-11. Annular groove 117 also serves as a demarcation between the end of proximal volume 158 and the beginning of middle volume 159, even though the volumes are fluidly connected. Opening 110 has an interior diameter preferably in a range of about 0.2069 inches to about 0.2089 inches, more preferably 0.2064 inches to about 0.2084 inches and most preferably about 0.2079 inches measured from the inner sealing member surface 109 of sealing member 108.

Tapered sidewall 130 comprises a lower sidewall 112, a middle sidewall 125, a sealing member 118 and a wall member 113. Lower sidewall 112 has a length measured from the annular groove 117 to the distal end that defines the combined length of the middle sidewall portion 105 and the distal sidewall portion 106. In the illustrated embodiment, proximal sidewall portion 104 comprises a wall member 113 and a sealing member 118 that extends from the top 141 of flange 108 toward the distal end 102. Wall member 113 and sealing member 118 join together at middle sidewall 125. The middle sidewall 125 and the wall member 113 have a combined length that defines the length of the proximal sidewall portion 104.

As shown in FIG. 6, an arcuate channel 115 is formed between a surface of both wall member 113 and flange 108 and a surface of sealing member 118. In one embodiment, wall member 113 extends to surface 141 without providing flange section 108. Flange 108 is provided to add additional thickness of material to strengthen and add additional surface area to contact the bottom of the pipette tool.

In operation, the bottom surface of the pipette tool travels in a direction from the proximal end 101 to the distal end 102, contacts the top surface 141 and continues travel after contacting surface 141. This operation separates the pipette tip from contact with the pipette tool shaft. Therefore, the top surface 141 of wall member 113, with or without flange 108, has a sufficient thickness and surface area to contact the bottom surface of a pipette tool during a pipette tip ejection procedure.

The diameter measured proximate from where the sealing member 118 and the wall member 113 split from sidewall 125, is essentially the same as the interior diameter 135 of opening 110, preferably in a range of about 0.2069 inches to about 0.2089 inches, more preferably 0.2064 inches to about 0.2084 inches and most preferably about 0.2079 inches. Essentially the same, in the context of any dimensions or measurements illustrated herein, is defined as within a tolerance of ±0.0005 inches. Therefore, the surface 109 of sealing member 118 forms an essentially cylindrical volume 180 relative to axis 103.

A second interior diameter 137, measured proximate where first tapered surface 111 begins, is preferably in a range of about 0.2031 inches to about 0.2051 inches, more preferably 0.2036 inches to about 0.2046 inches and most preferably about 0.2041 inches. Accordingly, the surface 120 is tapered from the proximal end 101 to the distal end 102 and as such, forms a first frustoconical volume 181 relative to axis 103. A third interior diameter 139 measured from the bottom of first tapered surface 111 at the annular groove 117 is preferably in a range of about 0.1783 inches to about 0.1803 inches, more preferably 0.1788 inches to about 0.1798 inches and most preferably about 0.1793 inches. As such, the first tapered surface 111 forms a third frustoconical volume relative to axis 103. In one embodiment, diameter 135 and 137 are essentially the same. Therefore, volumes 180, 181 would both be cylindrical.

First tapered surface 111 forms a stop means for limiting the travel of a shaft of a pipette tool toward the distal end 102 of pipette tip 100. In operation, the bottom of the pipette tool shaft would contact first tapered surface 111. First tapered surface 111 stops the movement of the shaft and prevents the surface of the shaft from contacting the inner surface below the annular groove 117. This function prevents the shaft from contacting a surface of lower sidewall 112, particularly, the liquid contents within middle volume 158. One skilled in the art will recognize that any structure may be used as a stop means such as a shelf having a horizontal surface instead of a first tapered surface 111 to contact the bottom of the shaft, a plurality of protuberances disposed on the inner surface of tapered sidewall 130 positioned in the proximal sidewall portion 104 or a circumferentially formed bump or ridge molded to be integral to the inner surface to name a few.

Figure 7:
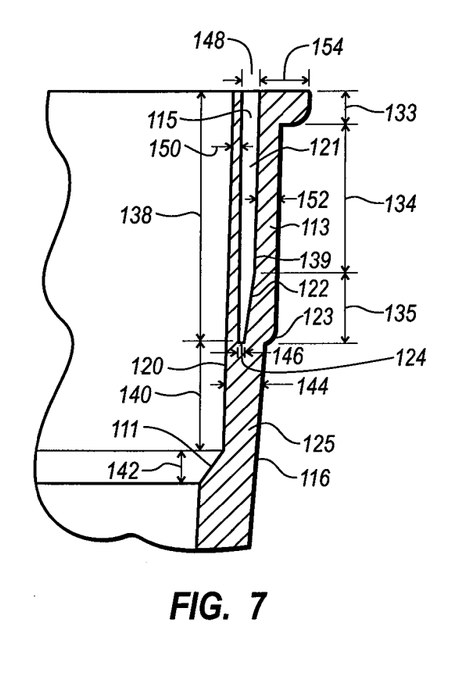
FIG. 7 is a detailed end view of the section of the pipette tip of FIG. 6.

The proximal sidewall portion is more particularly illustrated in the exploded partial cross-section view of FIG. 7. The measurements of the various thicknesses and lengths, all in inches, are also illustrated. Sealing member 118 has a sealing member channel surface 119 and an sealing member inner surface 109, as seen in FIG. 6. Sealing member 118 extends from the top 154 toward the distal end 102. Sealing member 118 has a cross sectional width 150 that is preferably in a range of about 0.0039 inches to about 0.0049 inches, more preferably 0.004 inches to about 0.0046 inches and most preferably about 0.0044 inches. Sealing member 118 has a length 138 that is preferably in a range of about 0.1510 inches to about 0.1490 inches, more preferably 0.1505 inches to about 0.1495 inches and most preferably about 0.1500 inches.

Wall member 113 comprises a wall member channel surface 139 and an outer wall member surface 107. In the illustrated embodiment, wall member 113 has a flange 108 that contacts the bottom surface of a pipette tool. However, flange 108 may be removed and wall member 115 has a flat outer surface from elbow portion 123 up to top 141. Wall member 113 has a cross sectional width 152 that is preferably in a range of about 0.0100 inches to about 0.0120 inches, more preferably 0.0105 inches to about 0.0115 inches and most preferably about 0.0110 inches. Wall member 113 has an overall length 133, 134, 135 that is preferably in a range of about 0.1510 inches to about 0.1490 inches, more preferably 0.1505 inches to about 0.1495 inches and most preferably about 0.1500 inches. Flange 108 has a width 133 that is preferably in a range of about 0.0180 inches to about 0.0200 inches, more preferably 0.0185 inches to about 0.0195 inches and most preferably about 0.0190 inches. Flange 108 has a length 154 that is preferably in a range of about 0.0265 inches to about 0.0285 inches, more preferably 0.0270 inches to about 0.0280 inches and most preferably about 0.0275 inches.

Channel 115 is defined between sealing member 118 and wall member 113. In the illustrated embodiment of FIG. 7, channel 115 has a height and width defined by the sealing member channel surface 119 and the wall member channel surface 139 having a straight surface segment 121 and a tapered surface segment 122 and a bottom surface 124 that joins the sealing member channel surface 119 and the tapered surface segment 122. Straight surface segment 121 has a length 134 that is preferably in a range of about 0.1096 inches to about 0.1116 inches, more preferably 0.1101 inches to about 0.1111 inches and most preferably about 0.1106 inches. Tapered surface segment 122 has a length 136 that is preferably in a range of about 0.0384 inches to about 0.0404 inches, more preferably 0.0389 inches to about 0.0399 inches and most preferably about 0.0394 inches. Bottom surface 124 has a length 146 that is preferably in a range of about 0.0043 inches to about 0.0053 inches, more preferably 0.045 inches to about 0.0051 inches and most preferably about 0.0048 inches. Channel 115 has a width 148 that is preferably in a range of about 0.0086 inches to about 0.0106 inches, more preferably 0.091 inches to about 0.0101 inches and most preferably about 0.0096 inches.

Middle sidewall 125 comprises a first tapered surface 111, a second tapered surface 120 and an outer surface 116. Middle sidewall has a cross sectional width 144 that is preferably in a range of about 0.0170 inches to about 0.0190 inches, more preferably 0.0175 inches to about 0.0185 inches and most preferably about 0.0180 inches. First tapered surface 120 has a length 140 that is preferably in a range of about 0.0650 inches to about 0.0670 inches, more preferably 0.0655 inches to about 0.0665 inches and most preferably about 0.0660 inches. Second tapered surface 120 has a length 142 that is preferably in a range of about 0.0114 inches to about 0.0134 inches, more preferably 0.0119 inches to about 0.0129 inches and most preferably about 0.0124 inches.

In the illustrated embodiment, channel 115 has a first channel section that is essentially rectangular in cross section defined between the straight surface segment 121 and a first portion of the sealing member channel surface 119. Channel 115 has a second channel section that is essentially trapezoidal in cross section defined between the tapered surface segment 122 and a second portion of the sealing member channel surface 119. Channel 115 may be take other shapes in addition to the illustrated cross sectional view shown in FIG. 7. For example, channel 115, in cross section, may be shaped like a triangle, rectangle, oval, circular, U-shaped or V-shaped to name a few.

Figure 8:
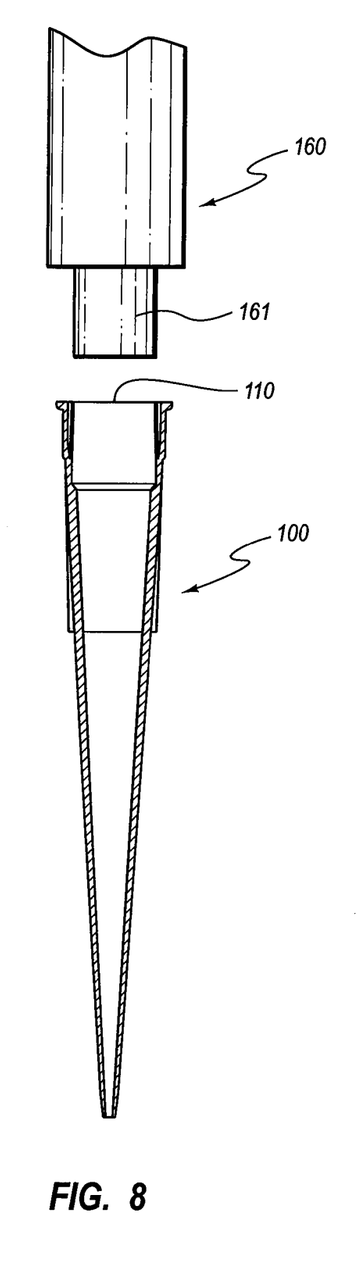
FIG. 8 is a front view of a pipette tip and pipette tool in accordance with the present invention.
Figure 9:
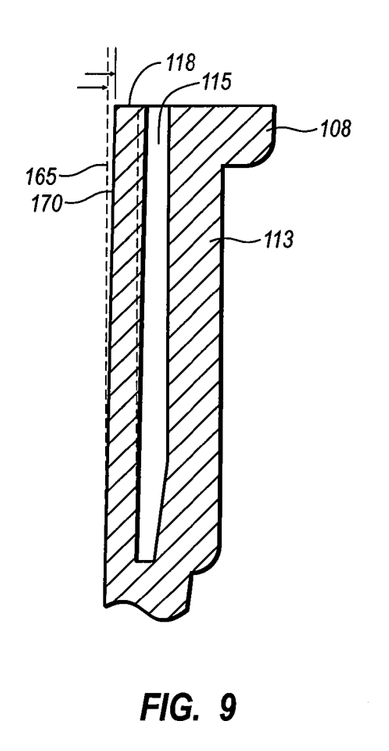
FIG. 9 is a detailed view of the pipette tip deflecting from a first position to a second position upon receiving a pipette tool.

In operation, the shaft 161 of pipette tool 160 is inserted into the opening 110, as shown in FIG. 8. The shaft of the pipette tool 160 causes sealing member 118 to deflect from a first position illustrated with dotted lines 165 to a second position illustrated with solid lines 170 in the direction of channel 115, as illustrated in FIG. 9. Simply stated, sealing member 118 is elastically deformable to frictionally effect a seal around the shaft 161 of pipette tool 160. The resulting seal prevents the liquid drawn into the interior volume of the pipette tip 100 from escaping past the shaft 161. Thus, pipette tip 100 allows for a more precise measurement of the amount of liquid drawn into the interior volume.

Figure 10:
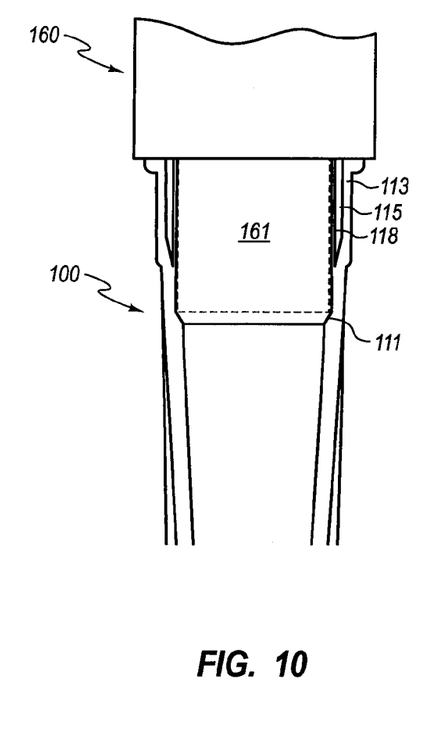
FIG. 10 is a front view of a pipette tool inserted into a pipette tip of the present invention.

The surface geometry of a shaft of a pipette tool determines the amount of surface area that contacts the sealing member 118. In FIG. 10, a cylindrical shaped shaft 161 of a pipette tool 160 is inserted into the opening of the pipette tip 100. Since shaft 161 is essentially cylindrical and the interior surface of sealing member 118 creates an essentially cylindrical opening, the surface of shaft 161 contacts the surface of sealing member 118 along its full length. Therefore, a seal is created between the two surfaces that extends the length of cylindrical shaft 161.

Figure 11:
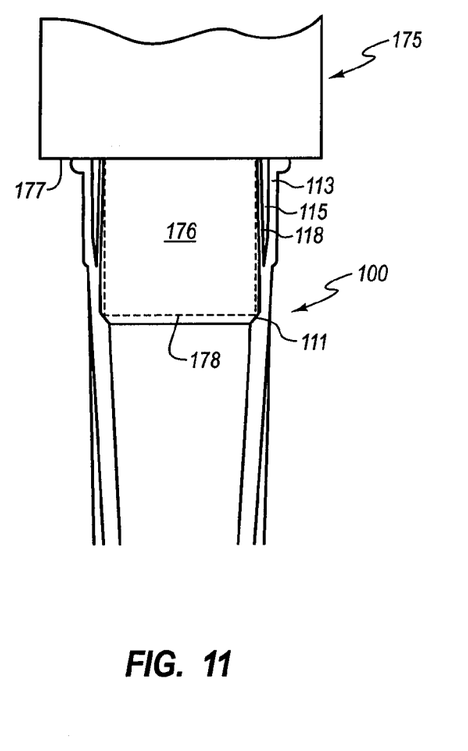
FIG. 11 is a front view of another embodiment of a pipette tool inserted into a pipette tip of the present invention.

In FIG. 11, a tapered shaft 176 of pipette tool 175 is inserted into the opening of the pipette tip 100. The shaft 176 of pipette tool 175 is tapered from the base of the pipette tool 177 to the tip 178. As shown, less than the entire surface of shaft 176 contacts the surface of sealing member 118. The contact between the surfaces creates a seal between the shaft 176 and the surface of the sealing member 118. However, since there is less surface area of contact between the shaft 176 and the sealing member 118, the amount of ejection force required to extract pipette tip 100 from pipette tool 175 is reduced. In both FIG. 10 and FIG. 11, a tapered segment 111, or stop means, limits the shaft from advancing toward the distal end of pipette tip 100.

Figure 12:
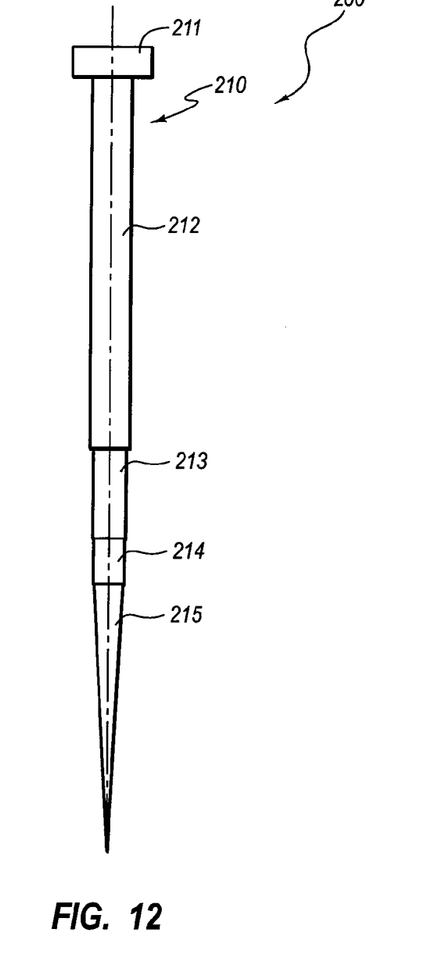
FIG. 12 is a perspective view of an inner molding apparatus in accordance with the present invention.
Figure 13:
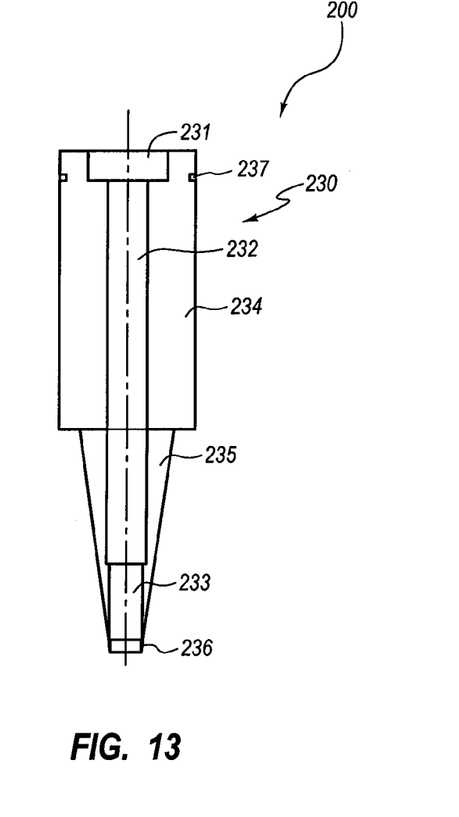
FIG. 13 is a cross-sectional view of an outer molding apparatus to be assembled with the inner molding apparatus illustrated in FIG. 12.

FIGS. 12-13 illustrate a molding apparatus 200 for molding a pipette tip in accordance with the present invention. The molding apparatus 200 is modified to provide the channel 29 in the pipette tip 10 and the channel 115 in pipette tip 100. FIG. 12 shows an inner molding apparatus 210, which is inserted into an outer molding apparatus 230 illustrated in FIG. 13. The inner molding apparatus 210 includes an upper block 211, a shaft portion 212, a fitting portion 213, a proximal portion 214 and a tip portion 215. The shaft portion 212 extends between the upper block 211 and the fitting portion 213. The proximal portion 214 extends between the fitting portion 213 and the tip portion 215. The proximal portion 214 is designed to form the inner wall 23 of the pipette tip 10 and the sealing member of pipette tip 100. The tip portion 215 is designed to form the inner wall of the lower sidewall 26, 112 and the tapered sidewall 51, 130.

The outer molding apparatus 230 includes an upper block recess 231, a shaft aperture 232 and a fitting aperture 233. The upper block recess 231 is formed to receive the upper block 211. The shaft aperture 232 is formed to receive the shaft portion. The fitting aperture 233 is formed to receive the fitting portion 213. The outer molding apparatus 230 also includes a main block portion 234 and a lower block portion 235. The lower block portion 235 is attached to the main block portion 234. The lower block portion 235 has a tapered shape. At the most distal end of the tapered shape and opposite the main block 234, a slot molding apparatus 236 is arranged on the lower block portion 235. The slot molding apparatus 236 is designed to form the channel 29 in the pipette tip 10 and the channel 115 in pipette tip 100.

The molding apparatus 200 is placed in a mold (not shown) and locked in place using a slip ring. The slip ring is inserted into a groove 237 formed in the main block portion 234. The mold is designed to form the outer surfaces of the pipette tip 10 and pipette tip 100. Thus, one skilled in the art would recognize that the inner surface of the mold would be designed to be the inverse shape of the outer surface of the pipette tip as shown in FIGS. 1 and 4.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pipette tip comprising:
a tapered sidewall having a proximal end, a distal end and a tapered sidewall length extending from said proximal end to said distal end, said tapered sidewall having an arcuate inner surface extending along said tapered sidewall length, said arcuate inner surface defining a volume with an axis, said axis extending from said proximal end to said distal end, said tapered sidewall having an upper portion for receiving a shaft of a pipette tool, said upper portion comprising:
a wall member having a wall member length, a wall member channel surface, an outer wall member surface, and a top surface joining said wall member channel surface and said outer wall member surface; and
a sealing member having a sealing member length, a sealing member channel surface, and a sealing member inner surface that is coextensive with at least a portion of said arcuate inner surface, said sealing member channel surface spaced radially towards said axis from said wall member channel surface to define an arcuate channel therein between, said arcuate channel extending from said top surface of said wall member toward said distal end, said sealing member being deflectable from a first position to a second position in the direction of said arcuate channel when receiving said shaft of said pipette tool, said sealing member being elastically deformable to frictionally effect a seal around said shaft of said pipette tool; and
a stop means for limiting the travel of said shaft of said pipette tool toward said distal end, said stop means being positioned in said upper portion.

2. The pipette tip of claim 1, wherein said stop means is located on said arcuate inner surface of said tapered sidewall at a distance closer to said distal end of said tapered sidewall than said sealing member, said stop means adapted to prevent said shaft from contacting said arcuate inner surface of said tapered sidewall between said distal end and said stop means.

3. The pipette tip of claim 1, wherein said sealing member length is proximate to said wall member length.

4. The pipette tip of claim 3, wherein said sealing member length is equal to said wall member length.

5. The pipette tip of claim 1, wherein said arcuate channel has a bottom surface joining said sealing member channel surface and said wall member channel surface.

6. The pipette tip of claim 5, wherein said wall member length and said sealing member length are measured from the top surface of said wall member relative to said bottom surface of said arcuate channel.

7. The pipette tip of claim 6, wherein said wall member channel surface has a straight surface segment and a tapered surface segment, wherein said tapered surface segment has a width defined by a distance from said outer wall member surface to said tapered surface segment in the radial direction, wherein said width increases from said proximal end to said distal end.

8. The pipette tip of claim 7, wherein said arcuate channel has a first channel section that is essentially rectangular in cross-section defined between said straight surface segment of said wall member channel surface and a first section of said sealing member channel surface located radially towards said axis and across from said straight surface segment and a second channel section that is essentially trapezoidal in cross-section defined between said tapered surface segment of said wall member channel surface and a second section of said sealing member channel surface located radially towards said axis and across from said tapered surface segment.

9. The pipette tip of claim 1, wherein the tapered sidewall further comprises an arcuate outer surface extending along said tapered sidewall length, said arcuate outer surface having a plurality of ribs disposed thereon spanning from said arcuate outer surface proximate to said upper portion of said tapered sidewall to a middle portion of said arcuate outer surface located closer to said distal end of said tapered sidewall than said upper portion, said plurality of ribs configured to strengthen said tapered sidewall.

10. A pipette tip comprising:
a tapered sidewall having a proximal end and a distal end and a tapered sidewall length extending from said proximal end to said distal end, said tapered sidewall having an arcuate inner surface extending along said tapered sidewall length, said arcuate inner surface defining a volume around an axis, said axis extending from said proximal end to said distal end, said tapered sidewall comprising:
a distal sidewall portion defining a tip, said tip having an aperture disposed therein, said distal sidewall portion having a tapered distal sidewall inner surface coextensive with at least a portion of said arcuate inner surface proximate said distal sidewall portion, said distal sidewall inner surface defining a conical-shaped volume relative to said center axis;
a middle sidewall portion having a tapered middle sidewall inner surface coextensive with at least a portion of said arcuate inner surface and contiguous with said distal sidewall inner surface, said tapered middle sidewall inner surface defining a first frusto-conical-shaped volume relative to said center axis, said middle sidewall portion having a middle sidewall outer surface and a plurality of ribs disposed thereon for strengthening said tapered sidewall and for contacting a surface of a pipette rack; and
a proximal sidewall portion for receiving a shaft of a pipette tool, said proximal sidewall portion having a proximal sidewall inner surface coextensive with at least a portion of said arcuate inner surface, said proximal sidewall inner surface having a tapered surface segment and a straight surface segment, said tapered surface segment defining a second frustoconical-shaped volume relative to said center axis and said straight surface segment defining a cylindrical-shaped volume relative to said center axis, said tapered surface segment being contiguous with said middle sidewall inner surface, said proximal sidewall portion adapted to receive said shaft of said pipette tool, said tapered surface segment configured to prevent said shaft from contacting said middle sidewall inner surface, said proximal sidewall portion comprising:
a wall member having a wall member length, a wall member channel surface, an outer wall member surface, and a top surface joining said wall member channel surface and said outer wall member surface, said wall member channel surface having a straight surface segment proximate said top surface and a tapered surface segment located distally from said straight surface segment; and a sealing member having a sealing member length, a sealing member channel surface, and a sealing member inner surface that is coextensive with at least a portion of said arcuate inner surface and at least a portion of said proximal sidewall inner surface, said sealing member channel surface spaced radially towards said axis from said wall member channel surface to define an arcuate channel therein between, said arcuate channel extending from said proximal end toward said distal end, said sealing member being deflectable from a first position to a second position in the direction of said arcuate channel when receiving said shaft of said pipette tool, said sealing member being elastically deformable to frictionally effect a seal around said shaft of said pipette tool, said arcuate channel having a first channel section that is essentially rectangular in cross-section defined between said straight surface segment of said wall member channel surface and a first section of said sealing member channel surface located radially towards said axis and across from said straight surface segment and a second channel section that is essentially trapezoidal in cross-section defined between said tapered surface segment of said wall member channel surface and a second section of said sealing member channel surface located radially towards said axis and across from said tapered surface segment.

11. The pipette tip of claim 10, wherein said tapered surface segment of said wall member channel surface has a width defined by a distance from said outer wall member surface to said tapered surface segment in the radial direction, wherein said width increases from said proximal end to said distal end.

* * * * *